US010478669B2

(12) United States Patent
Chen (10) Patent No.: US 10,478,669 B2
(45) Date of Patent: Nov. 19, 2019

(54) EXERCISE MOTION TRACKING ASSEMBLY, EXERCISE MOTION TRACKING SYSTEM, AND METHODS OF USE THEREOF

(71) Applicant: JENKINS ASIA TECH (SHANGHAI) LIMITED, Shanghai (CN)

(72) Inventor: Weng Kin Chen, Shanghai (CN)

(73) Assignee: Jenkins Asia Tech (Shanghai) Limited (CN)

( * ) Notice: Subject to any disclaimer, the term of this patent is extended or adjusted under 35 U.S.C. 154(b) by 227 days.

(21) Appl. No.: 15/829,401

(22) Filed: Dec. 1, 2017

(65) Prior Publication Data

US 2018/0154213 A1 Jun. 7, 2018

Related U.S. Application Data

(60) Provisional application No. 62/430,254, filed on Dec. 5, 2016.

(51) Int. Cl.
| | |
|---|---|
| *A61B 5/01* | (2006.01) |
| *A63B 24/00* | (2006.01) |
| *A61B 5/0205* | (2006.01) |
| *A61B 5/00* | (2006.01) |
| *A61B 5/053* | (2006.01) |
| *A61B 5/22* | (2006.01) |
| *A61B 5/11* | (2006.01) |

(52) U.S. Cl.
CPC ........ *A63B 24/0062* (2013.01); *A61B 5/0017* (2013.01); *A61B 5/01* (2013.01); *A61B 5/0205* (2013.01); *A61B 5/0531* (2013.01); *A61B 5/0537* (2013.01); *A61B 5/11* (2013.01); *A61B 5/22* (2013.01); *A61H 2230/04* (2013.01); *A61H 2230/50* (2013.01); *A61H 2230/65* (2013.01); *A63B 2220/17* (2013.01); *A63B 2220/24* (2013.01); *A63B 2220/44* (2013.01); *A63B 2220/51* (2013.01); *A63B 2220/70* (2013.01); *A63B 2220/803* (2013.01); *A63B 2220/836* (2013.01)

(58) Field of Classification Search
CPC ..... A63B 24/0062; A61B 5/0017; A61B 5/01; A61B 5/0205
USPC ....................................... 73/379.01
See application file for complete search history.

(56) References Cited

U.S. PATENT DOCUMENTS

2016/0325143 A1* 11/2016 Yuen .................... G01P 7/00

* cited by examiner

*Primary Examiner* — Jamel E Williams
(74) *Attorney, Agent, or Firm* — Levine Bagade Han LLP (57) ABSTRACT

An exercise motion tracking assembly, an exercise motion tracking system, and a method of electronically tracking exercise motion are disclosed. In one embodiment, the exercise motion tracking assembly can comprise a base unit comprising a plurality of trigger columns and a tracker comprising a plurality of column ports, a plurality of switching components, and a plurality of sensors. At least one of the plurality of sensors can be activated when the tracker is detachably coupled to the base unit, causing at least one of the plurality of trigger columns to extend through at least one of the plurality of column ports and actuate at least one of the plurality of switching components.

20 Claims, 8 Drawing Sheets

EXERCISE MOTION TRACKING ASSEMBLY, EXERCISE MOTION TRACKING SYSTEM, AND METHODS OF USE THEREOF

CROSS-REFERENCE TO RELATED APPLICATION

This application claims the benefit of U.S. Provisional Patent Application No. 62/430,254 filed on Dec. 5, 2016, the content of which is hereby incorporated by reference in its entirety.

FIELD OF TECHNOLOGY

The present disclosure relates generally to the field of exercise equipment for strength, agility, or power training, and, more specifically, to an exercise motion tracking assembly, system, and methods of use thereof.

BACKGROUND

Modern portable client devices such as smartphones, smartwatches, and exercise monitors are providing increasing levels of functionality to support modern life, including storing and analyzing exercise or health data collected from users of such portable client devices. However, traditional methods of acquiring such health and exercise data involve manually entering such data into a portable client device through an interface screen of a mobile software application or carrying around a portable client device while exercising or engaging in physical movements or motions. Manually entering exercise or health data is often cumbersome, time-consuming, and difficult to sustain as a habit. In addition, carrying a portable client device while engaging in intensive exercise regimens such as cross-fit training or suspension band training can result in damage to such portable client devices or impair motions or movements involved with such exercise regimens. Moreover, as exercise equipment has evolved beyond traditional free weights to non-traditional equipment such as kettlebells, resistance bands or straps, weight bags, weight vests, and training ropes, the ability to monitor and record biomechanical and physiological data associated with the usage of such non-traditional equipment is becoming increasingly important.

Given the drawbacks of current exercise data collection techniques and equipment, a solution is needed which can collect exercise or health data without hindering one's exercise range of motion and which is compatible with an assortment of different types of equipment. Such a solution should also be cost-effective to manufacture and able to withstand wear and tear in the course of usage.

SUMMARY

An exercise motion tracking assembly, an exercise motion tracking system and methods of using such assemblies and systems are disclosed. In one embodiment, an exercise motion tracking assembly comprises a base unit and a tracker. The base unit can comprise a tracker engagement side and an equipment engagement side. The tracker engagement side can comprise a plurality of attachment arms and a plurality of trigger columns extending or protruding out from the tracker engagement side.

The tracker can comprise a tracker housing and a base engagement panel having a plurality of column ports. The tracker housing can engage with the base engagement panel to enclose a printed circuit board (PCB), a plurality of sensors coupled to the PCB, a microcontroller unit (MCU) coupled to the PCB, a plurality of switching components coupled to the PCB, and a rechargeable battery configured to power the MCU and the plurality of sensors.

The tracker is configured to be detachably coupled to the base unit by the plurality of attachment arms. At least one of the plurality of sensors can be activated when the tracker is detachably coupled to the base unit causing at least one of the plurality of trigger columns to extend through at least one of the plurality of column ports and actuate at least one of the plurality of switching components. The switching components can be configured to switch on or activate the plurality of sensors by supplying current to the plurality of sensors. The switching components can also be configured to switch on communication buses or functionalities associated with the storage or transmission of data collected by the sensors.

In one embodiment, the base unit can comprise at least three trigger columns. In other embodiments, the base unit can comprise between two and ten trigger columns. The number of column ports on the base engagement panel can be greater than the number of trigger columns on the base unit.

In one embodiment, the base engagement panel can comprise at least three column ports. In other embodiments, the base engagement panel can comprise between two and ten column ports. In some embodiments, the number of trigger columns on the base unit can exceed the number of column ports on the base engagement panel. In other embodiments, the number of column ports on the base engagement panel can exceed the number of trigger columns.

The tracker can be configured to rotate clockwise or counterclockwise with respect to the base unit such that at least one of the trigger columns on the base unit is aligned with one of the column ports on the tracker and the at least one of the trigger columns on the base unit is aligned with another one of the column ports on the tracker when the tracker is rotated with respect to the base unit.

At least one of the plurality of trigger columns can be depressible into the tracker engagement side. A trigger column can be depressed or pushed back into the tracker engagement side by a portion of the base engagement panel. A portion of each of the plurality of trigger columns can also comprise or be composed of a conductive material.

The plurality of sensors can comprise a multi-axis inertial motion sensor, an optical heart rate sensor, a galvanic skin response (GSR) sensor, a bio-impedance sensor, an ambient light sensor, a UV sensor, or any combination thereof. The tracker can also comprise a GPS unit. The GPS unit can also be activated when the tracker is detachably coupled to the base unit causing at least one of the plurality of trigger columns to extend through at least one of the plurality of column ports and actuate at least one of the plurality of switching components.

The tracker further comprises a memory unit to store data collected by the plurality of sensors and a wireless communication unit to wirelessly transmit data collected by the plurality of sensors to a client device. The wireless communication unit can be a Bluetooth™ module, a general packet radio service (GPRS) module, a GSM module, a WiFi module, or a combination thereof.

The equipment engagement side of the base unit can be configured to detachably couple to a portion of an exercise apparatus. The equipment engagement side can be a side of the base unit opposite the tracker engagement side. The equipment engagement side can comprise a clip, a hook-and-loop fastener, a buckle, a strap, or a combination thereof.

An exercise motion tracking system is also disclosed. The exercise motion tracking system can comprise a tracker and a plurality of base units including at least a first base unit and a second base unit.

The first base unit can comprise a plurality of first attachment arms, a first tracker engagement side, and a plurality of first trigger columns arranged on the first tracker engagement side in a first arrangement.

The second base unit can comprise a plurality of second attachment arms, a second tracker engagement side, and a plurality of second trigger columns arranged on the second tracker engagement side in a second arrangement. The second arrangement can be different from the first arrangement meaning that the arrangement of the second trigger columns on the first tracker engagement side can be different from the arrangement of the first trigger columns on the second tracker engagement side.

The exercise motion tracking system can comprise a tracker configured to detachably coupled to any of the plurality of base units including the first base unit and the second base unit. The tracker can comprise a tracker housing and a base engagement panel having a plurality of column ports. The tracker housing can engage with the base engagement panel to enclose a printed circuit board (PCB), a plurality of sensors coupled to the PCB, a microcontroller unit (MCU) coupled to the PCB, a plurality of switching components coupled to the PCB, and a rechargeable battery configured to power the MCU and the plurality of sensors.

In one embodiment, a subset of the plurality of sensors on the tracker can be activated when the tracker is detachably coupled to the first base unit by the first attachment arms. Coupling the tracker to the first base unit can cause at least one of the plurality of first trigger columns to extend through at least one of the plurality of column ports and actuate at least one of the plurality of switching components.

In this and other embodiments, another subset of the plurality of sensors on the tracker can be activated when the tracker is detachably coupled to the second base unit by the second attachment arms. Coupling the tracker to the second base unit causes at least one of the plurality of second trigger columns to extend through at least one of the plurality of column ports and actuate at least one of the plurality of switching components.

At least one of the plurality of first trigger columns is depressible into the first tracker engagement side and at least one of the plurality of second trigger columns is depressible into the second tracker engagement side. A trigger column can be depressed or pushed back into the tracker engagement side by a portion of the base engagement panel.

A method of electronically tracking exercise motion is further disclosed. The method can include coupling a first equipment engagement side of a first base unit to a portion of a first exercise apparatus. The method can further involve coupling a tracker to the first base unit by securing the tracker with the plurality of first attachment arms. A subset of the plurality of sensors can be activated when the tracker is coupled to the first base unit. Coupling the tracker to the first base unit can cause at least one of the plurality of first trigger columns to extend through at least one of the plurality of column ports and actuate at least one of the plurality of switching components.

The method can also include rotating the tracker clockwise or counterclockwise with respect to the first base unit to actuate different switching components and different sensors, wherein at least one of the trigger columns on the first base unit is aligned with one of the column ports on the tracker and the at least one of the trigger columns on the first base unit is aligned with another one of the column ports on the tracker when the tracker is rotated with respect to the first base unit.

The method can further include detaching the tracker from the first base unit and coupling a second equipment engagement side of a second base unit to a portion of a second exercise apparatus. The method can further involve coupling the tracker to the second base unit by securing the tracker with the plurality of second attachment arms. In this embodiment, another subset of the plurality of sensors can be activated when the tracker is coupled to the second base unit. Coupling the tracker to the second base unit can cause at least one of the plurality of second trigger columns to extend through at least one of the plurality of column ports and actuate at least one of the plurality of switching components.

The method can further involve storing data collected by the plurality of sensors in a memory unit of the tracker and transmitting data collected by the plurality of sensors to a client device using a wireless communication unit of the tracker.

DETAILED DESCRIPTION

Figure 1:
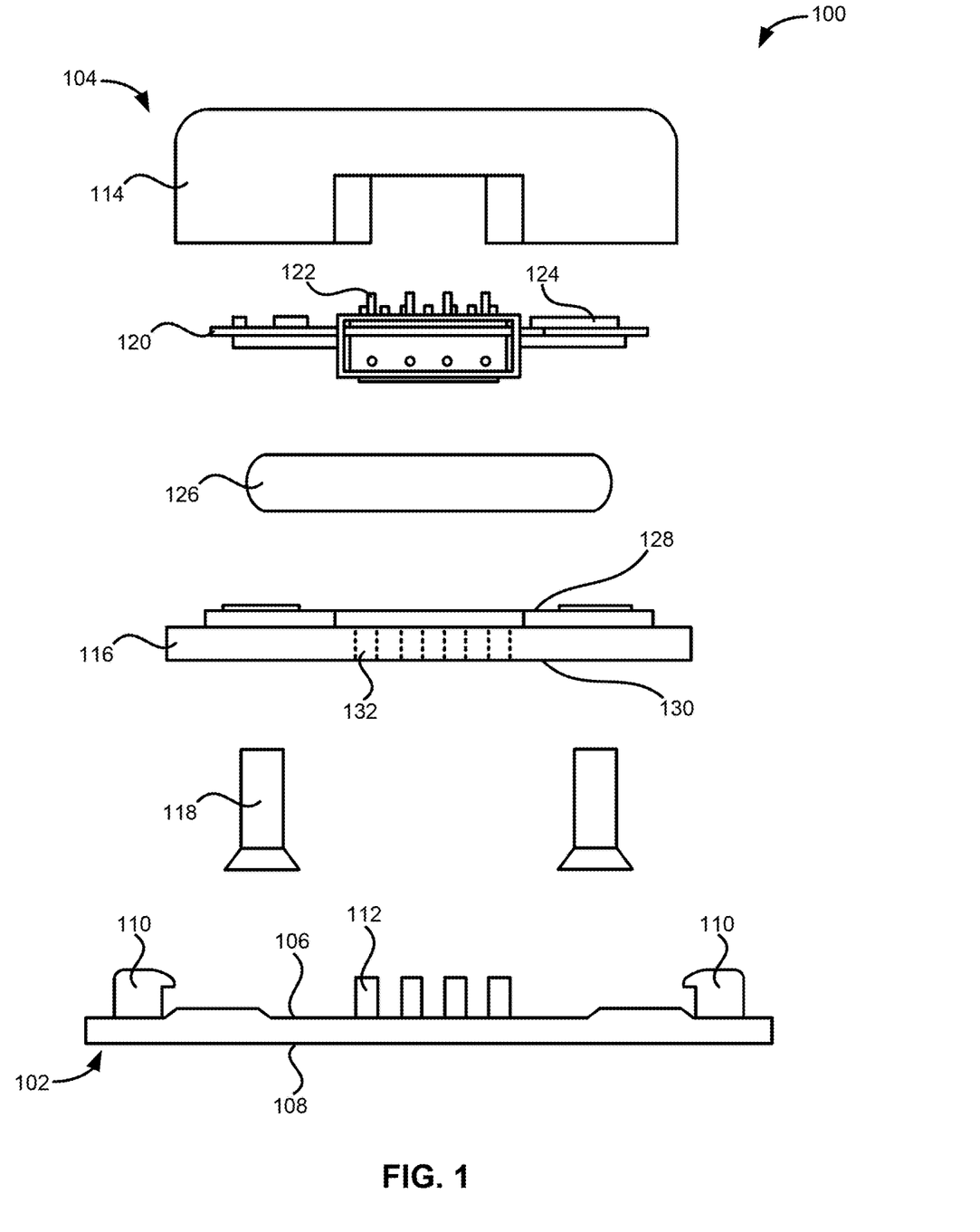
FIG. 1 illustrates an exploded view of one embodiment of an exercise motion tracking assembly.

FIG. 1 illustrates an exploded view of one embodiment of an exercise motion tracking assembly 100. The exercise motion tracking assembly 100 can comprise a base unit 102 and a tracker 104.

The tracker 104 can be configured to detachably couple to base unit 102. In one embodiment, the tracker 104 can be detachably coupled to the base unit 102 by an interference fit, a clip mechanism, a hook-and-loop fastening mechanism, or a combination thereof.

The base unit 102 can comprise a tracker engagement side 106 and an equipment engagement side 108. The tracker engagement side 106 can comprise a plurality of attachment arms 110 and a plurality of trigger columns 112. The plurality of attachment arms 110 can detachably grasp the sides of the tracker 104 to couple to the tracker 104. Each of the plurality of attachment arms 110 can comprise an overhang to hold or pin down a portion of the tracker 104.

In one embodiment, at least part of the attachment arms 110 can be part of or contiguous with the tracker engagement side 106. The attachment arms 110 can be composed of or comprise a polymer, a metal, or a combination thereof. The attachment arms 110 can be flexible or rigid. For example, as shown in FIG. 1, the base unit 102 can comprise two attachment arms 110 separated from one another by a space or surface for receiving the tracker 104.

In one embodiment, the trigger columns 112 can be protrusions or protuberances extending out from the tracker engagement side 106. For example, the trigger columns 112 can be substantially cylindrical protrusions or protuberances extending out from the tracker engagement side 106. The trigger columns 112 can be orthogonal or perpendicular to the tracker engagement side 106 when the trigger columns 112 are fully extended or unobstructed. In one embodiment, the trigger columns 112 can originate from within the base unit 102 and extend out through one or more bores or openings along the tracker engagement side 106.

A portion of each of the plurality of trigger columns 112 can also comprise or be composed of a conductive material such as a conductive metal or semiconducting material. For example, a tip or terminal end of each of the plurality of trigger columns 112 can comprise or be composed of a conductive material. In some embodiments, at least one of the trigger columns 112 can be configured to depress into the body of the base unit 102. In other embodiments, at least part of each of the plurality of trigger columns 112 can collapse flat (e.g., through a telescoping mechanism) or flush with the surface of the tracker engagement side 106 when the trigger column 112 is pressed against a surface of a device or object.

As shown in FIG. 1, the tracker 104 can comprise a tracker housing 114 and a base engagement panel 116 configured to engage with or couple to the tracker housing 114 via screws 118 or other attachments or fasteners.

The tracker 104 can also comprise a printed circuit board (PCB) 120, a plurality of sensors 122 coupled to the PCB 120, a microcontroller unit (MCU) 124 coupled to the PCB 120, a plurality of switching components 600 (see FIG. 6) coupled to the PCB 120, and a rechargeable battery 126 configured to supply power to the MCU 124 and the plurality of sensors 122. The rechargeable battery 126 can be a rechargeable lithium-ion battery.

The tracker housing 114 can engage with the base engagement panel 116 to enclose the PCB 120, the plurality of sensors 122, the MCU 124, the plurality of switching components 600, and the rechargeable battery 126.

The base engagement panel 116 can comprise an interior side 128 and an exterior side 130. The exterior side 130 can physically contact at least a portion of the tracker engagement side 106 of the base unit 102 when the tracker 104 is detachably coupled to the base unit 102 by the plurality of attachment arms 110. The interior side 128 of the base engagement panel 116 can be contained within the tracker housing 114 when the base engagement panel 116 is coupled to the tracker housing 114.

The base engagement panel 116 can also comprise a plurality of column ports 132. The column ports 132 can be openings, channels, or exposed areas having at least one outlet or port opening along the surface of the exterior side 130 of the base engagement panel 116. In some embodiments, the column ports 132 can extend entirely through the base engagement panel 116 from the exterior side 130 to the interior side 128.

The column ports 132 can act as an entry way or access channel to the interior of the tracker 104. For example, the column ports 132 can be aligned with a portion of the PCB 120 and at least a portion of the PCB 120 can be accessed through one or more of the column ports 132.

As will be discussed in the following sections, at least one of the plurality of sensors 122 can be activated when the tracker 104 is detachably coupled to the base unit 102 causing at least one of the plurality of trigger columns 112 to extend through at least one of the plurality of column ports 132 and actuate at least one of the plurality of switching components 600 (see FIG. 6) within the tracker 104. In certain embodiments, the switching components 600 can be configured to switch on or activate the plurality of sensors 122 by supplying current to the plurality of sensors 122. In this and other embodiments, the switching components 600 can also be configured to switch on communication buses or functionalities associated with the storage or transmission of data collected by the plurality of sensors 122.

Figure 2A:
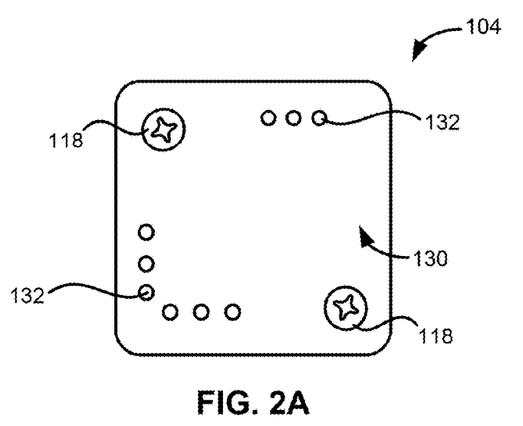
FIG. 2A illustrates a top view of a base engagement panel of one embodiment of a tracker of the exercise motion tracking assembly.

FIG. 2A illustrates a top view of an exterior side 130 of the base engagement panel 116 of a tracker 104, in one or more embodiments. As shown in FIG. 2A, the base engagement panel 116 can be substantially square-shaped having rounded corners. The column ports 132 can be arranged near one or more corners or edges of the base engagement panel 116. In some embodiments, the column ports 132 can be offset from the edges of the base engagement panel 116 by a distance ranging from 3.0 mm to 7.00 mm.

As shown in FIG. 2A, the column ports 132 can have a substantially circular port opening. In some embodiments, the port opening of each of the column ports 132 can have a diameter of between approximately 2.0 mm and 5.0 mm.

In the embodiment shown in FIG. 2A, at least some of the column ports 132 can be arranged in a substantially L-shaped pattern near a corner of the base engagement panel 116. For example, as shown in FIG. 2A, six column ports 132 can be arranged in a substantially L-shaped pattern at one corner of the base engagement panel 116. In this same embodiment, three additional column ports 132 can be arranged in one horizontal line or file near another corner of the base engagement panel 116 diagonal to the aforementioned corner. In other embodiments not shown in the figures, the column ports 132 can be arranged in multiple L-shaped patterns near two or more corners of the base engagement panel 116.

The column ports 132 can be arranged in various patterns or configurations. For example, the column ports 132 can be arranged in a circular pattern, a rectangular pattern, a triangular pattern, a zig-zag pattern, a star pattern, a row-and-column pattern, a linear pattern, an X-pattern, or a combination thereof.

In some embodiments, the base engagement panel 116 can comprise at least three column ports 132. In other embodiments, the base engagement panel 116 can comprise between two and ten column ports 132. In certain embodiments, the number of column ports 132 on the base engagement panel 116 exceeds the number of trigger columns 112 on a base unit 102. One benefit of this design is the ability to use the same tracker 104 with multiple base units 102 where each of the base units 102 comprises a different arrangement of trigger columns 112. In these and other embodiments, at least one of the column ports 132 can spatially align with at least one of the trigger columns 112 on the base unit 102 such that at least one of the trigger columns 112 can extend through or into the at least one of the column ports 132 when the tracker 104 is coupled to the base unit 102.

Figure 2B:
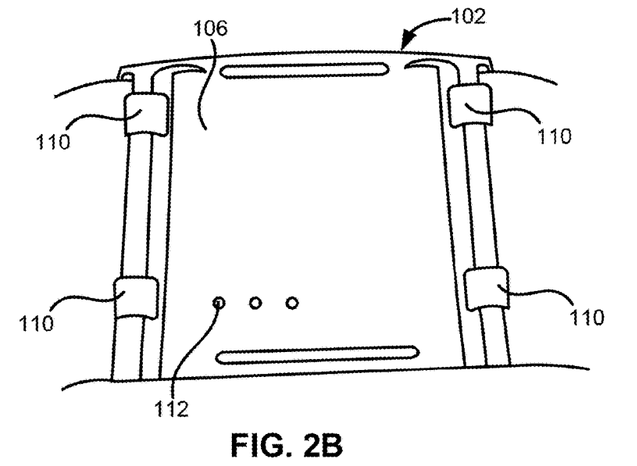
FIG. 2B illustrates a top view of a tracker engagement side of one embodiment of a base unit of the exercise motion tracking assembly.

FIG. 2B illustrates a top view of a tracker engagement side 106 of a base unit 102 of one embodiment of the exercise motion tracking assembly 100. A plurality of trigger columns 112 can extend out from the tracker engagement side 106. As shown in FIG. 2B, three trigger columns 112 can be aligned linearly along one edge of the base unit 102. In other embodiments not shown in FIG. 2B, the base unit 102 can comprise two trigger columns 112 or between four and ten trigger columns 112.

The trigger columns 112 can be arranged such that at least one of the column ports 132 on the tracker 104 can be aligned with at least one of the trigger columns 112 when the tracker 104 is coupled to the base unit 102 by the attachment arms 110. In this way, the trigger column 112 can extend into or through the aligned column port 132 and actuate at least one of the switching components 600 within the tracker 104.

The trigger columns 112 can be arranged in various patterns or configurations. For example, the trigger columns 112 can be arranged in a circular pattern, a rectangular pattern, a triangular pattern, a zig-zag pattern, a star pattern, a row-and-column pattern, a linear pattern, an X-pattern, or a combination thereof. In some embodiments, the arrangement of trigger columns 112 can match the arrangement of column ports 132 on the base engagement panel 116 of the tracker 104. In other embodiments, the arrangement of trigger columns 112 can be different from the arrangement of column ports 132 on the base engagement panel 116 of the tracker 104.

In some embodiments, the number of trigger columns 112 on each of the base units 102 can match the number of column ports 132 on the tracker 104. In other embodiments, the number of trigger columns 112 on each of the base units 102 can differ from the number of column ports 132 on the tracker 104.

Figure 2C:
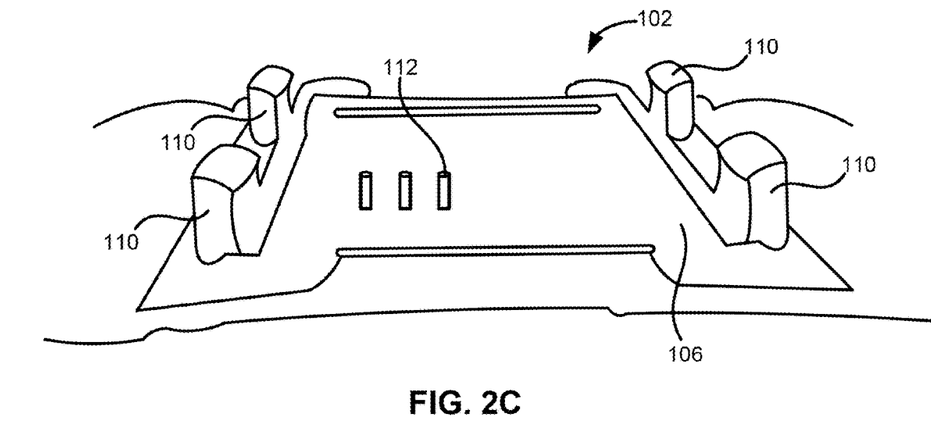
FIG. 2C illustrates a side perspective view of the tracker engagement side of one embodiment of the base unit.

FIG. 2C illustrates a side perspective view of the tracker engagement side 106 of the base unit 102 of FIG. 2B. As shown in the example embodiment of FIG. 2C, the trigger columns 112 can be cylindrical rods extending orthogonally out from the tracker engagement side 106. In other embodiments, the trigger columns 112 can be cuboidal, dome-shaped, or pyramidal.

As shown in FIG. 2C, the three trigger columns 112 can extend into the three column ports 132 along the bottom edge of the tracker 104 when the tracker 104 is coupled to the base unit 102. Although not shown in FIG. 2C, in certain embodiments, the number of trigger columns 112 on the base unit 102 can exceed the number of column ports 132 on the tracker 104.

Figure 2D:
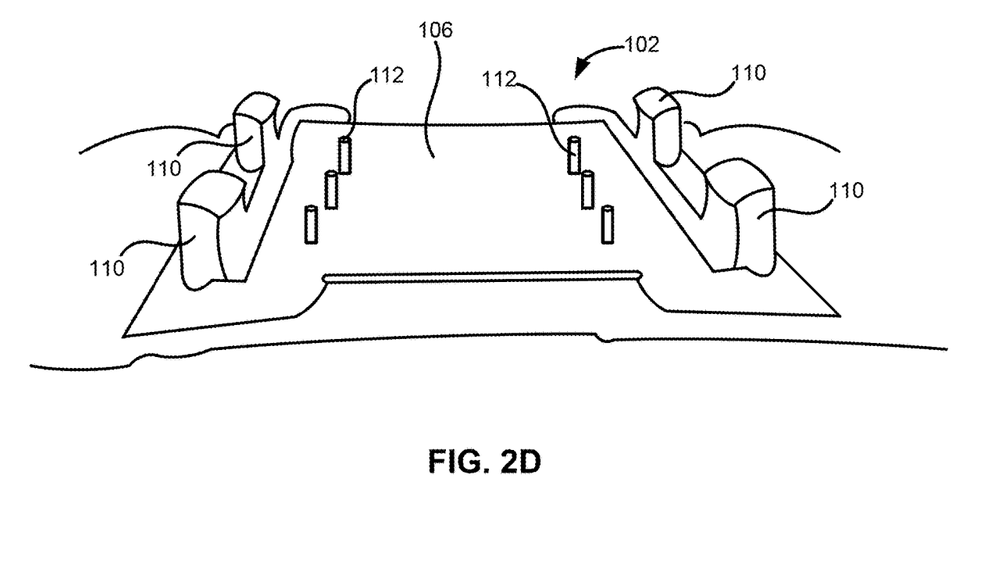
FIG. 2D illustrates a side perspective view of the tracker engagement side of another embodiment of the base unit.

FIG. 2D depicts a side perspective view of the tracker engagement side 106 of another embodiment of the base unit 102 different from that shown in FIG. 2C. When coupled with the tracker 104 depicted in FIG. 2A, the trigger columns 112 of the base unit 102 of FIG. 2D can actuate different switching components 600 within the tracker 104 than the ones actuated by the base unit 102 of FIGS. 2B and 2C.

FIG. 2D also illustrates that the number or arrangement of trigger columns 112 on a particular portion of the base unit 112 can differ from the number or arrangement of column ports 132 located on the matching or corresponding portion of the tracker 104. For example, the base unit 102 shown in FIG. 2D can have three trigger columns 112 arranged vertically along one lateral side of the tracker engagement side 106 and three additional trigger columns 112 arranged vertically along the other lateral side. When coupled with the tracker 104 depicted in FIG. 2A, only two of the six trigger columns 112 on the base unit can extend into or through the column ports 132 of the tracker 104. As such, the remaining four trigger columns 112 can be temporarily depressed or pushed back into the tracker engagement side 106 of the base unit 102 by the base engagement panel 116.

The trigger columns 112 can be depressible so as to allow trackers 104 with different arrangements of column ports 132 to couple to base units 102 with different arrangements of trigger columns 112. In some embodiments, the trigger columns 112 can be supported or biased by one or more springs such that the trigger columns 112 are extended orthogonally out of the tracker engagement side 106 by the one or more springs. In these and other embodiments, the trigger columns 112 can collapse into the tracker engagement side 106 by contracting the springs or through a telescoping mechanism.

It is contemplated by this disclosure that the tracker 104 can be rotated clockwise or counterclockwise such that the same tracker 104 can couple with the same base unit 102 in different ways. The tracker 104 can be configured to rotate clockwise or counterclockwise with respect to the base unit 102 such that at least one of the trigger columns 112 on the base unit 102 is aligned with one of the column ports 132 on the tracker 104 and the at least one of the trigger columns 112 on the base unit 102 is aligned with another one of the column ports 132 on the tracker 104 when the tracker 104 is rotated with respect to the base unit 102. For example, the tracker 104 can be rotated clockwise or counterclockwise between 45 and 325 degrees and still able to couple with the same base unit 102. In these embodiments, the tracker 104 and the tracker engagement side 106 of the base unit 102 are preferably symmetrically-shaped such as, but not limited to, radially symmetric circles or symmetric polygons. Rotating the tracker 104 with respect to the base unit 102 can allow different trigger columns 112 on the base unit 102 to actuate or activate different sensors or switching components within the same tracker 104. One benefit of this design is being able to take advantage of the different functionalities offered by the tracker 104 by simply rotating the tracker 104 with respect to the base unit 102.

Figure 3:
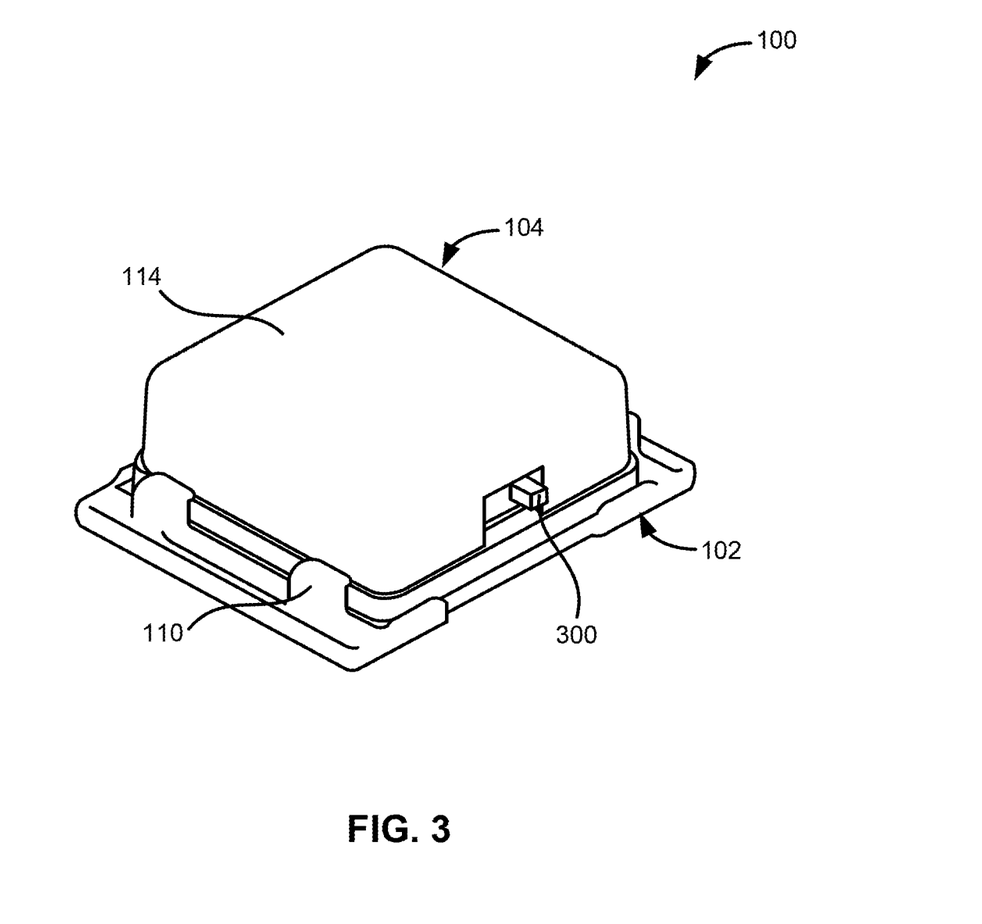
FIG. 3 illustrates a perspective view of the tracker detachably coupled to the base unit.

FIG. 3 illustrates a perspective view of the tracker 104 detachably coupled to the base unit 102. As shown in FIG. 3, the tracker 104 can be detachably coupled to the base unit 102 when the attachment arms 110 grasp or otherwise secure one or more sides of the tracker 104. Although not shown in the figures, it is also contemplated by this disclosure that the tracker 104 can be detachably coupled to the base unit 102 by magnets attached to either the tracker 104, the base unit 102, or a combination thereof. The magnets can be any type of ferromagnetic material or metal capable of magnetically attaching to a complementary ferromagnetic metal or material. For example, the magnets can comprise permanent magnets, ferrite magnets, ceramic magnets, rare-earth magnets, or a combination thereof. As a more specific example, the magnets can comprise a neodymium iron boron (NdFeB or NIB) magnet, a samarium cobalt (SmCo) magnet, or an aluminum nickel cobalt (Alnico) magnet.

As shown in FIG. 3, the tracker housing 114 can be a substantially square-shaped housing having rounded corners. The tracker 104 can also comprise a toggle switch 300 for turning the tracker 104 on or off.

Figure 4A:
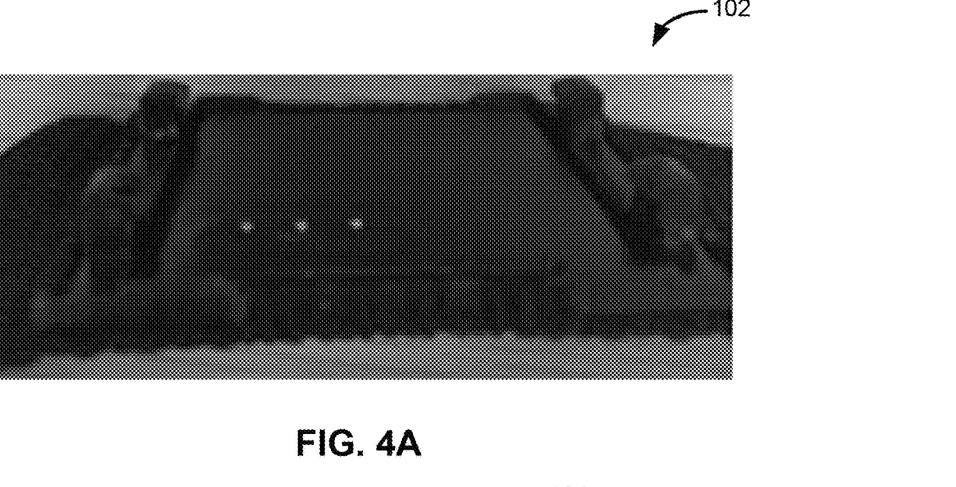
FIG. 4A is a black-and-white image of an embodiment of the base unit.

FIG. 4A is a black-and-white image of an embodiment of the base unit 102. In one embodiment, the base unit 102 can be composed of or comprise a polymer, a metal, or a combination thereof. For example, the base unit 102 can be fabricated from or comprise acrylonitrile butadiene styrene (ABS) plastic, polypropylene, polycarbonate, polyvinyl chloride (PVC), thermoplastic rubber, nitrile butadiene rubber, or a combination thereof.

Figure 5A:
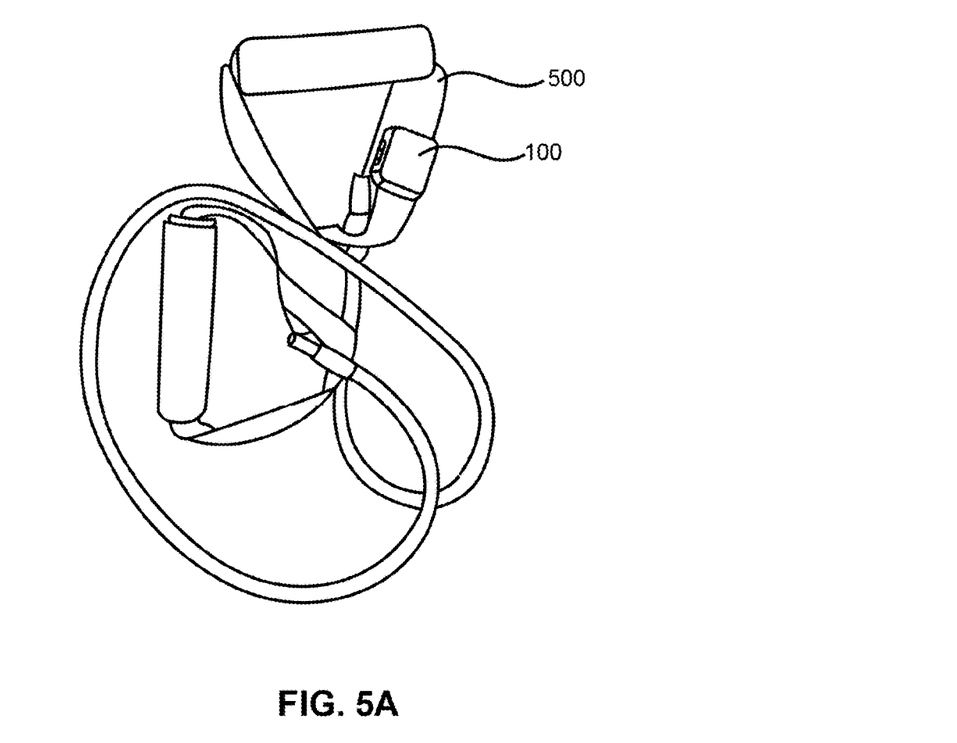
FIG. 5A is a black-and-white image of an embodiment of a tracker detachably coupled to a base unit detachably coupled to an exercise apparatus.
Figure 5B:
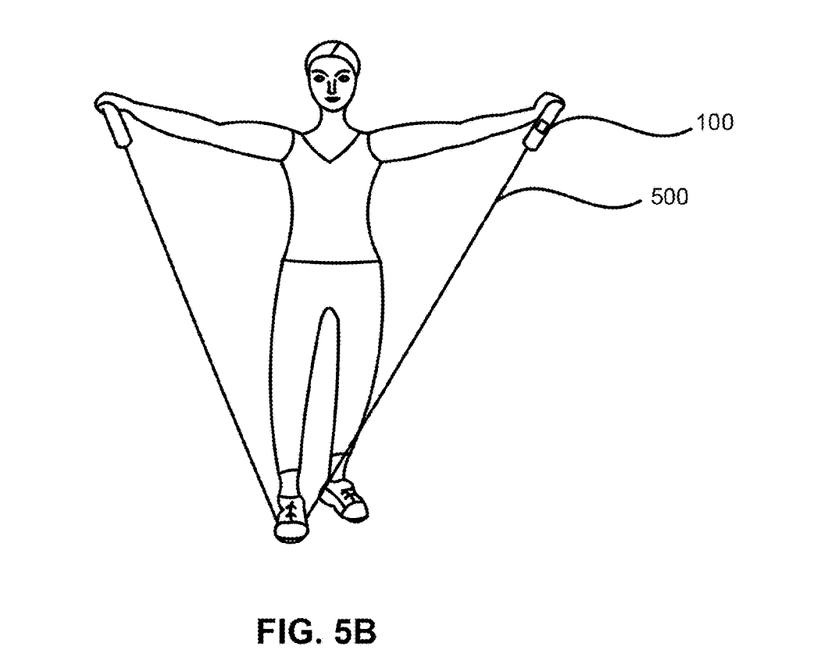
FIG. 5B is a black-and-white image of a user using the exercise apparatus of FIG. 5A.

The base unit 102 can be configured to detachably couple to a portion of an exercise apparatus 500 (e.g., the exercise apparatus of FIGS. 5A and 5B). The base unit 102 can detachably couple to the exercise apparatus 500 via clips, straps, hook-and-loop fasteners, pins, or a combination thereof. In some embodiments, the base unit 102 can include a rigid portion fabricated from a polymeric or metallic material and a flexible portion fabricated from a synthetic fabric. The rigid portion can be secured to the flexible portion by stitches, adhesives, mechanical fasteners, or a combination thereof. The synthetic fabric can include nylon, polyester, elastane, or a combination thereof. More specifically, the nylon can be Cordura® nylon, oxford cloth nylon, or a combination thereof. The flexible portion can more easily allow the base unit 102 to detachably couple to straps or bands of the exercise apparatus 500.

Figure 4B:
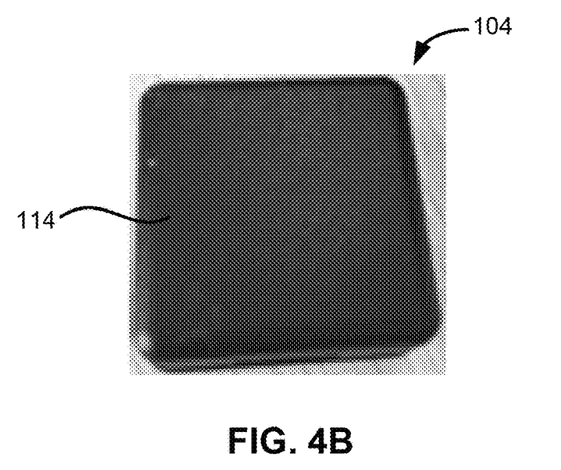
FIG. 4B is a black-and-white image of a tracker housing of an embodiment of the tracker.

FIG. 4B is a black-and-white image of a tracker housing 114 of an embodiment of the tracker 104. The tracker housing 114 can be a rigid housing fabricated from a polymeric material, a metallic material, or a combination thereof. For example, the tracker housing 114 can be fabricated from or comprise ABS plastic, polypropylene, polycarbonate, PVC, thermoplastic rubber, nitrile butadiene rubber, or a combination thereof. In other example embodiments, the tracker housing 114 can be fabricated from or comprise stainless steel.

The tracker housing 114 can be configured to protect the inner components of the tracker 104 including the PCB 120, the plurality of sensors 122, the MCU 124, the battery 126, or a combination thereof from unintentional damage or routine stress and wear.

As shown in FIG. 4B, the tracker housing 114 can be shaped as a substantially square cuboid having rounded corners and edges. In some embodiments, the tracker housing 114 can have a length or width dimension of between approximately 30.0 mm and 50.0 mm. In these and other embodiments, the tracker housing 114 can also have a height dimension of between approximately 10.0 mm and 25.0 mm.

Figure 4C:
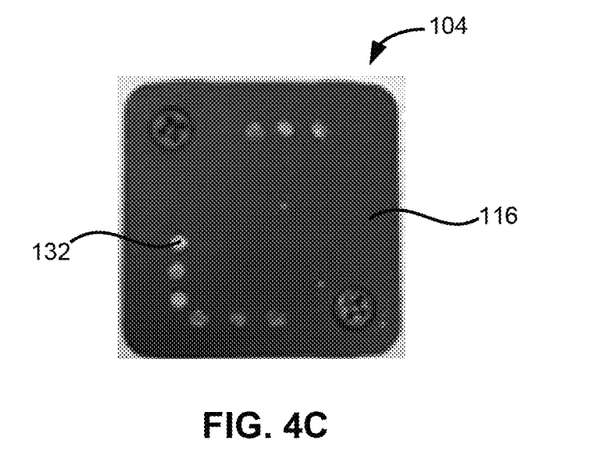
FIG. 4C is a black-and-white image of a base engagement panel of an embodiment of the tracker.

FIG. 4C is a black-and-white image of the exterior side 130 of the base engagement panel 116 of an embodiment of the tracker 104. As shown in FIG. 4C, at least some of the column ports 132 can be arranged in a substantially L-shaped pattern. The column ports 132 arranged in the L-shaped pattern can be positioned near a first corner of the base engagement panel 116. In this embodiment, additional column ports 132 can be arranged linearly near a second corner of the base engagement panel 116 diagonal from the first corner.

Also, as shown in FIG. 4C, the exterior side 130 of the base engagement panel 116 can be substantially flat, which allows the tracker 104 to more easily couple to the tracker engagement side 106 of the base unit 102. In other embodiments, the exterior side 130 of the base engagement panel 116 can have grooves, divots, or indentations along the surface of the exterior side 130.

FIG. 5A is a black-and-white image of an embodiment of the exercise motion tracking assembly 100 coupled to an exercise apparatus 500. As shown in FIG. 5A, the exercise apparatus 500 can be a resistance band having a pair of handles. The equipment engagement side 108 of the base unit 102 can be configured to detachably couple to a portion of one of the handles. For example, the handles can be composed of or comprise a synthetic fabric such as Cordura® nylon. In one embodiment, the equipment engagement side 108 can comprise a clasp or clip for detachably coupling to the fabric of one of the handles. In other embodiments, a part of the fabric handle can be thread through belt loops or slots defined along the equipment engagement side 108 of the tracker 104. In additional embodiments, the equipment engagement side 108 of the base unit 102 can be detachably coupled to the exercise apparatus 500 by hook-and-loop fasteners such as Velcro™.

The equipment engagement side 108 of the base unit 102 can be configured to detachably couple to a portion of the exercise apparatus 500. The equipment engagement side 108 can be a side of the base unit 102 opposite the tracker engagement side 106. The equipment engagement side 108 can comprise a clip, a hook-and-loop fastener, a buckle, a strap, or a combination thereof.

FIG. 5B is a black-and-white image of a user using the exercise apparatus 500 of FIG. 5A. As shown in FIG. 5B, the exercise apparatus 500 can be a resistance band having a pair of handles and the exercise motion tracking assembly 100 can be detachably coupled to one of the handles of the resistance band.

In some embodiments, the exercise motion tracking assembly 100 can be part of an exercise motion tracking system. The exercise motion tracking system can comprise at least one interchangeable tracker 104 and a plurality of base units 102 including at least a first base unit and a second base unit. For example, the first base unit can be the base unit 102 shown in FIGS. 2B and 2C and the second base unit can be the base unit 102 shown in FIG. 2D.

The first base unit can comprise a plurality of first attachment arms, a first tracker engagement side, and a plurality of first trigger columns arranged on the first tracker engagement side in a first arrangement. For example, the first trigger columns can be arranged on the first tracker engagement side in an arrangement similar to the one shown in FIGS. 2B and 2C.

The second base unit can comprise a plurality of second attachment arms, a second tracker engagement side, and a plurality of second trigger columns arranged on the second tracker engagement side in a second arrangement. The second arrangement can be different from the first arrangement meaning that the arrangement of the second trigger columns on the first tracker engagement side can be different from the arrangement of the first trigger columns on the second tracker engagement side. For example, the second trigger columns can be arranged on the second tracker engagement side in an arrangement similar to the one shown in FIG. 2D.

In these embodiments, a subset of the plurality of sensors 122 on the tracker 104 can be activated when the tracker 104 is detachably coupled to the first base unit by the first attachment arms. For example, coupling the tracker 104 to the first base unit can cause at least one of the plurality of first trigger columns to extend through at least one of the plurality of column ports 132 on the tracker and actuate at least one of the plurality of switching components 600 (see FIG. 6) within the tracker 104. The switching components 600 can, in turn, activate or turn on a subset of the plurality of sensors 122.

For example, when the tracker 104 is coupled to an instance of the base unit 102 attached to the resistance band of FIGS. 5A and 5B, one or more trigger columns 112 on the base unit 102 can extend through one or more column ports 132 on the tracker 104 to actuate one or more switching components 600 responsible for activating a multi-axis inertial motion sensor (e.g., a multi-axis accelerometer and gyroscope) and an optical heart rate sensor within the tracker 104.

In addition, another subset of the plurality of sensors 122 on the tracker 104 can be activated when the tracker 104 is detachably coupled to the second base unit by the second attachment arms. Coupling the tracker 104 to the second base unit can cause at least one of the plurality of second trigger columns to extend through at least one of the plurality of column ports and contact at least one of the plurality of switching components 600 within the tracker 104. The switching components 600 can, in turn, activate or turn on another subset of sensors 122.

For example, a user can detach the tracker 104 from the instance of the base unit 102 attached to the resistance band and couple the tracker 104 to another instance of the base unit 102 coupled to a running armband. By doing so, one or more trigger columns 112 on the base unit 102 attached to the running armband can extend through one or more different column ports 132 on the tracker 104 to actuate one or more different switching components 600 responsible for activating a GPS unit, a UV sensor, and an ambient light sensor within the tracker 104.

In additional embodiments, the tracker 104 can detach from a base unit 102 and be rotated clockwise or counter-clockwise between approximately 45 degrees and 320 degrees (depending on the geometry or shape of the tracker 104 and the base unit 102) and coupled once again to the same base unit 102. Doing so can change the positional arrangement of the trigger columns 112 on the base unit 102 relative to the column ports 132 on the tracker 104, thereby allowing different combinations of the trigger columns 112 to extend through the aligned column ports 132 and actuate different switching components 600 in order to activate different sensors 122 within the tracker 104.

The tracker 104 can be coupled to a base unit 102 detachably coupled to, but is not limited to, a suspension band, a bracelet, a headband, a chest strap, a heart rate monitor, a free weight, a weight plate, a barbell, a dumbbell, a kettlebell, a medicine or weight bag, a strength training rope, or any combination thereof. Although not shown in the figures, it is contemplated by this disclosure that the tracker 104 of FIGS. 1, 2A, 3, 4B, and 4C, the base unit 102 of FIGS. 1, 2B, 2C, 2D, 3, and 4A, and the PCB of FIG. 6 can be configured and designed to work with any of the aforementioned exercise apparatus or exercise equipment.

Figure 6:
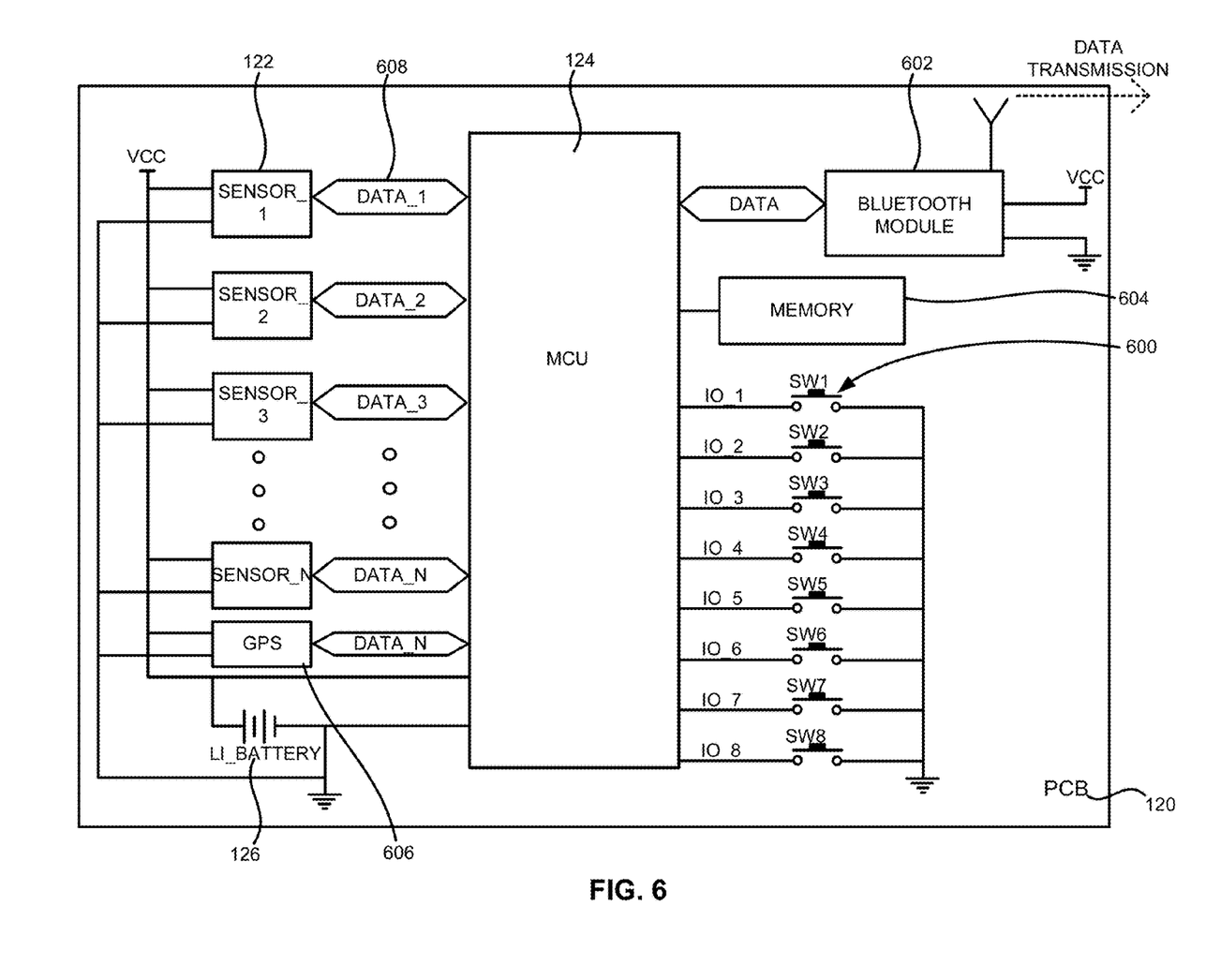
FIG. 6 illustrates a schematic of certain electrical components of the tracker.

FIG. 6 illustrates a schematic of certain electrical components of the tracker 104 electrically coupled to a PCB 120. The PCB 120 can be secured within the tracker housing 114 or coupled by screws 118 to a portion of the base engagement panel 116. The PCB 120 can be electrically coupled to the MCU 124, the plurality of sensors 122, a plurality of switching components 600, a wireless communication unit 602, a memory unit 604, and a rechargeable battery 126.

The plurality of sensors 122 can comprise a multi-axis inertial motion sensor such as a 3-axis gyroscope, a 3-axis accelerometer, and a 3-axis magnetometer, an optical heart rate sensor, a galvanic skin response (GSR) sensor, a bio-impedance sensor, an ambient light sensor, a UV sensor, or any combination thereof. The tracker can also comprise a GPS unit 606.

The plurality of sensors 122 and the GPS unit 606 can collect data 608 concerning the motion of the tracker 104, the orientation of the tracker 104, the geographic location of the tracker 104, or a combination thereof. For example, when the sensors 122 include a multi-axis inertial motion sensor such as a 3-axis accelerometer and a 3-axis gyroscope, the inertial motion sensor can collect data concerning the acceleration or the change in orientation of the tracker 104. When the tracker 104 is coupled to a base unit 102 coupled to an exercise apparatus 500, the plurality of sensors 122 can also collect data concerning the motion or movement of the exercise apparatus 500. The plurality of sensors 122 can also collect data 608 concerning a physiological condition of the user. For example, when the sensors 122 comprise a bio-impedance sensor or a galvanic skin response (GSR) sensor, the user can touch or otherwise contact a portion of the tracker 104 serving as an electrode or contact for the sensor 122.

Any of the sensors 122 can transmit the data 608 collected to the MCU 124 or to the memory unit 604 to be stored. The MCU 124 can also be programmed to transmit the data 608 collected by any of the sensors 122 to a client device using the wireless communication unit 602. In one embodiment, the MCU 124 can comprise a 32-bit processor such as an ARM™ processor. For example, the MCU 124 can comprise a Cortex™ processor. The memory unit 604 can comprise a nonvolatile storage such as a non-volatile random access memory (NVRAM), flash memory, a volatile storage such as static random access memory (SRAM), or a combination thereof.

The wireless communication unit 602 can be a Bluetooth™ module, a general packet radio service (GPRS) module, a GSM module, a WiFi module, or a combination thereof. The client device can be any mobile computing or personal electronic device comprising at least a processor, a wireless communication interface, a memory, and a display. In one embodiment, the client device can be a smartphone of a user of the exercise motion tracking assembly 100 or a user of the exercise motion tracking system. In other embodiments, the client device can comprise a laptop computer, a smartwatch, a fitness tracker, a desktop computer, an entertainment device, a smart television, or a combination thereof.

One or more sensors 122 or the GPS unit 606 can be activated when one or more trigger columns 112 of the base unit 102 extends through the column ports 132 on the base engagement panel 116 of the tracker 104 to actuate one or more switching components 600 electrically coupled to the sensors 122 or the GPS unit 606. In some embodiments, activating the sensors 122 or the GPS unit 606 can involve delivering power or allowing current to flow to the sensors 122 or the GPS unit 606. In other embodiments, activating the sensors 122 can comprise storing data 608 collected by the sensors 122 or the GPS unit 606 or transmission of data 608 collected by the sensors 122 or the GPS unit 606 via the wireless communication unit 602 to the client device.

The switching components 600 can be embedded on the PCB 120 or coupled to the MCU 124 via one or more I/O ports, interfaces, or controllers. The switching components 600 can comprise push-to-make or normally-open switches, push-to-break or normally-closed switches, or any combination thereof. For example, the switching components 600 can be a plurality of single pole single throw (SPST) momentary switches, single pole double throw (SPDT)

switches, single pole changeover (SPCO) switches, or any combination thereof. The switching components 600 can also comprise one or more microelectromechanical systems.

In some embodiments, a portion of each of the trigger columns 112 can be composed of or comprise a conductive material and the trigger column 112 can directly act as a switch to bridge contacts of the switching components 600. In other embodiments, the trigger columns 112 can contact or actuate other components on the PCB 120 coupled to the switching components 600 to actuate the switching components 600.

As previously mentioned, actuating different switching components 600 or different combinations of switching components 600 can activate different subsets of sensors 122 or the GPS unit 606. For example, the MCU 124 can be programmed by its firmware to activate an accelerometer when a first switching component 600 is actuated and activate a UV sensor when a second switching component 600 and a third switching component 600 are actuated simultaneously. The association between sensors 122 and switching components 600 can be pre-programmed into the firmware of the MCU 124 and can be updated via updates to the firmware. The MCU 124 can also comprise or be coupled to an analog-to-digital converter (ADC) configured to convert analog signals collected by one or more sensors 122 to digital signals.

In some embodiments, all of the sensors 122 and the GPS unit 606 can continuously be in operation when the tracker 104 is powered on via the toggle switch 300. In these embodiments, activating the sensor 122 or the GPS unit 606 can involve instructing the MCU 124 to transmit data 608 collected by a particular sensor 122 or the GPS unit 606 to a client device wirelessly connected to the tracker 104 via the wireless communication unit 602.

Figure 7:
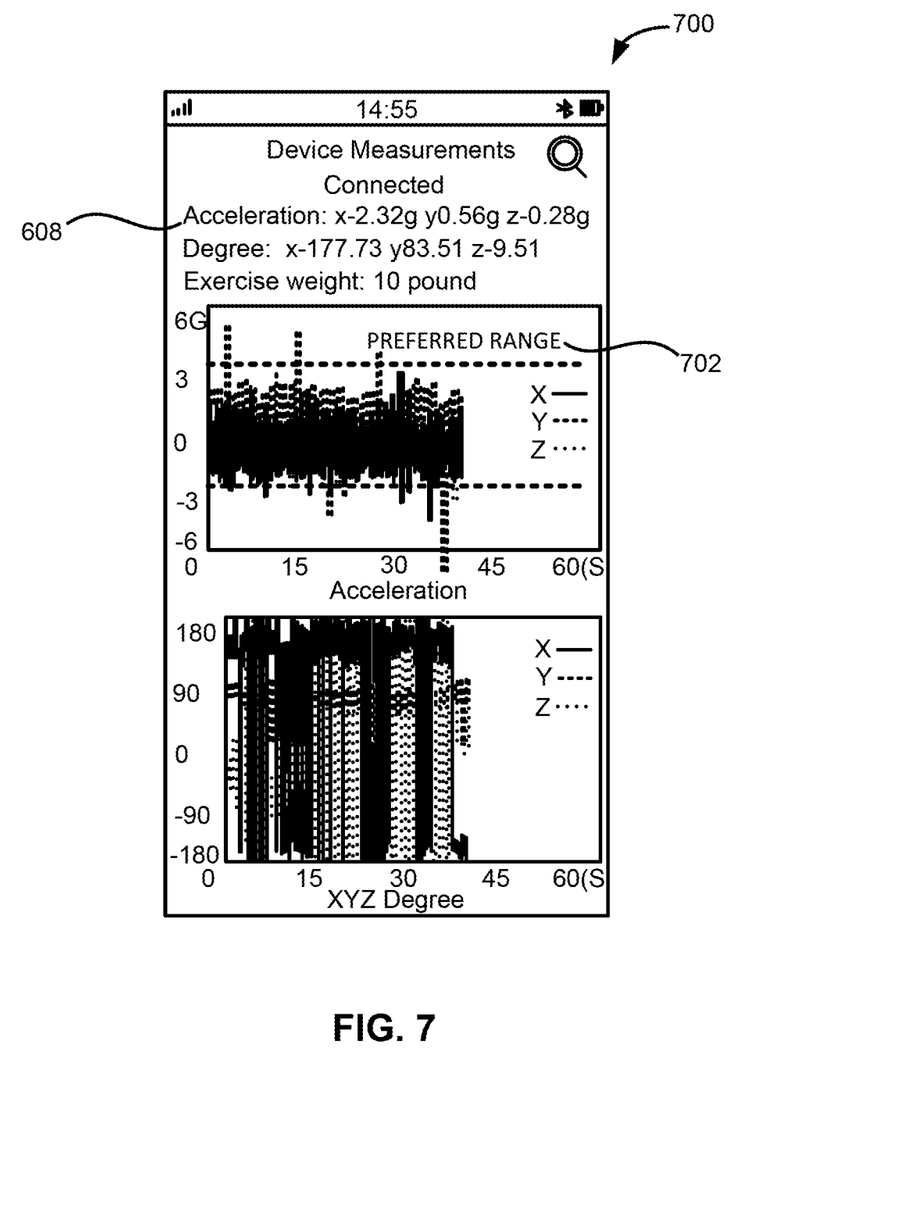
FIG. 7 is a black-and-white image of a graphical user interface of a mobile software application run on a client device in wireless communication with the tracker.

FIG. 7 is a black-and-white image of a graphical user interface (GUI) 700 of a mobile software application run on a client device in wireless communication with the tracker 104. For example, the client device can be a smartphone carried by a user of an exercise apparatus 500 having a base unit 102 and the tracker 104 detachably coupled to the exercise apparatus 500. As shown in FIG. 7, the GUI 700 can depict the data 608 collected by one or more sensors 122 or the GPS unit 606 within the tracker 104 in numerical form or through one or more rendered graphs or charts.

In some embodiments, the exercise motion tracking system can comprise the base unit 102, the tracker 104, and the mobile software application running on the client device. The mobile software application can be instructions executed by one or more processors of the client device instructing the one or more processors to process signals or data received from the tracker 104. For example, the mobile software application can include instructions to convert analog signals received from one or more sensors 122 to digital signals. Also, for example, the mobile software application can include instructions to render the data 608 collected by the sensors 122 as graph or chart GUIs.

As shown in FIG. 7, the mobile software application can also include instructions to display a preferred range 702 for the motion or movement data collected by the tracker 104. For example, a user can work out with a resistance band having a base unit 102 coupled to a handle of the resistance band. The user can detachably couple a tracker 104 to the base unit 102 in such an orientation such that the trigger columns 112 on the base unit 102 extend through certain column ports 132 and actuate certain switching components 600 that, in turn, activate a 3-axis accelerometer and a 3-axis gyroscope within the tracker 104. The user can then perform a lateral arm raise exercise using the resistance band. As the user performs the exercises, a Bluetooth™ module within the tracker 104 can wirelessly transmit data 608 collected by the 3-axis accelerometer and the 3-axis gyroscope to a client device carried by the user. A mobile software application running on the client device can then render the data 608 collected by the 3-axis accelerometer and the 3-axis gyroscope in graph or chart form through one or more application GUIs. In one such application GUI, a recommended preferred range 702 for the user's acceleration when undertaking such an exercise can be rendered alongside the real-time data 608 collected by the 3-axis accelerometer and the 3-axis gyroscope within the tracker 104.

Although not shown in the figures, it is contemplated by this disclosure that a user can perform any variety of strength-training, plyometric, or cardio exercises by attaching the exercise motion tracking assembly 100 to a portion of an exercise apparatus 500 capable of being translated, displaced, carried, or otherwise moved by a user.

Each of the individual variations or embodiments described and illustrated herein has discrete components and features which may be readily separated from or combined with the features of any of the other variations or embodiments. Modifications may be made to adapt a particular situation, material, composition of matter, process, process act(s) or step(s) to the objective(s), spirit or scope of the present invention.

Methods recited herein may be carried out in any order of the recited events that is logically possible, as well as the recited order of events. Moreover, additional steps or operations may be provided or steps or operations may be eliminated to achieve the desired result.

It will be understood by one of ordinary skill in the art that all or a portion of the methods disclosed herein may be embodied in a non-transitory machine readable or accessible medium comprising instructions readable or executable by a processor or processing unit of a client device or the tracker 104.

Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, and equivalents of the variations or embodiments described herein. Further, the scope of the disclosure fully encompasses other variations or embodiments that may become obvious to those skilled in the art in view of this disclosure.

I claim:

1. An exercise motion tracking assembly, comprising:
a base unit comprising a tracker engagement side and an equipment engagement side,
wherein the tracker engagement side comprises a plurality of attachment arms and a plurality of trigger columns on the tracker engagement side; and
a tracker comprising a base engagement panel having a plurality of column ports, a printed circuit board (PCB), a plurality of sensors coupled to the PCB, a microcontroller unit (MCU) coupled to the PCB, a plurality of switching components coupled to the PCB, a rechargeable battery configured to power the MCU and the plurality of sensors, and a tracker housing configured to engage with the base engagement panel to enclose the PCB, the plurality of switching components, the plurality of sensors, the MCU, and the rechargeable battery,
wherein the tracker is configured to be detachably coupled to the base unit by the plurality of attachment arms, and
wherein at least one of the plurality of sensors is activated when the tracker is detachably coupled to the base unit causing at least one of the plurality of trigger columns to extend through at least one of the plurality of column ports and actuate at least one of the plurality of switching components.

2. The exercise motion tracking assembly of claim 1, wherein the base unit comprises at least three trigger columns and the base engagement panel comprises at least three column ports, and wherein the number of column ports on the base engagement panel is greater than the number of trigger columns on the base unit.

3. The exercise motion tracking assembly of claim 1, wherein the plurality of sensors comprise any combination of a multi-axis inertial motion sensor, an optical heart rate sensor, a galvanic skin response (GSR) sensor, a bio-impedance sensor, an ambient light sensor, and a UV sensor.

4. The exercise motion tracking assembly of claim 1, wherein the tracker further comprises a memory unit to store data collected by the plurality of sensors.

5. The exercise motion tracking assembly of claim 1, wherein the tracker is configured to rotate clockwise or counterclockwise with respect to the base unit such that at least one of the trigger columns on the base unit is aligned with one of the column ports on the tracker and the at least one of the trigger columns on the base unit is aligned with another one of the column ports on the tracker when the tracker is rotated with respect to the base unit.

6. The exercise motion tracking assembly of claim 1, wherein the equipment engagement side of the base unit is configured to detachably couple to a portion of an exercise apparatus.

7. The exercise motion tracking assembly of claim 1, wherein at least one of the plurality of trigger columns is depressible into the tracker engagement side.

8. The exercise motion tracking assembly of claim 1, wherein at least a portion of each of the plurality of trigger columns is composed of or comprises a conductive material.

9. An exercise motion tracking system, comprising:
a first base unit comprising a plurality of first attachment arms, a first tracker engagement side, and a plurality of first trigger columns arranged on the first tracker engagement side in a first arrangement;
a second base unit comprising a plurality of second attachment arms, a second tracker engagement side, and a plurality of second trigger columns arranged on the second tracker engagement side in a second arrangement different from the first arrangement;
a tracker comprising a base engagement panel having a plurality of column ports, a printed circuit board (PCB), a plurality of sensors coupled to the PCB, a microcontroller unit (MCU) coupled to the PCB, a plurality of switching components coupled to the PCB, a rechargeable battery configured to power the MCU and the plurality of sensors, and a tracker housing configured to engage with the base engagement panel to enclose the PCB, the plurality of sensors, the MCU, the plurality of switching components, and the rechargeable battery,
wherein a subset of the plurality of sensors are activated when the tracker is detachably coupled to the first base unit by the first attachment arms causing at least one of the plurality of first trigger columns to extend through at least one of the plurality of column ports and actuate at least one of the plurality of switching components, and
wherein another subset of the plurality of sensors are activated when the tracker is detachably coupled to the second base unit by the second attachment arms causing at least one of the plurality of second trigger columns to extend through at least one of the plurality of column ports and actuate at least one of the plurality of switching components.

10. The exercise motion tracking system of claim 9, wherein the plurality of sensors comprises any combination of a multi-axis inertial motion sensor, an optical heart rate sensor, a galvanic skin response (GSR) sensor, a bio-impedance sensor, an ambient light sensor, and a UV sensor.

11. The exercise motion tracking system of claim 9, wherein the tracker is configured to rotate clockwise or counterclockwise with respect to the first base unit such that at least one of the trigger columns on the first base unit is aligned with one of the column ports on the tracker and the at least one of the trigger columns on the first base unit is aligned with another one of the column ports on the tracker when the tracker is rotated with respect to the first base unit.

12. The exercise motion tracking system of claim 9, wherein the tracker further comprises a wireless communication unit to wirelessly transmit data collected by the plurality of sensors to a client device and a memory unit to store data collected by the plurality of sensors.

13. The exercise motion tracking system of claim 9, wherein at least one of the plurality of first trigger columns is depressible into the first tracker engagement side and at least one of the plurality of second trigger columns is depressible into the second tracker engagement side.

14. The exercise motion tracking system of claim 9, wherein at least a portion of each of the plurality of first trigger columns or each of the plurality of second trigger columns is composed of or comprises a conductive material.

15. A method of electronically tracking exercise motion, comprising:

coupling a first equipment engagement side of a first base unit to a portion of a first exercise apparatus, wherein the first base unit further comprises a first tracker engagement side opposite the first equipment engagement side and the first tracker engagement side comprises a plurality of first attachment arms, a first tracker engagement side, and a plurality of first trigger columns arranged on the first tracker engagement side in a first arrangement; and coupling a tracker to the first base unit by securing the tracker with the plurality of first attachment arms, wherein the tracker comprises a base engagement panel having a plurality of column ports, a printed circuit board (PCB), a plurality of sensors coupled to the PCB, a microcontroller unit (MCU) coupled to the PCB, a plurality of switching components coupled to the PCB, a rechargeable battery configured to power the MCU and the plurality of sensors, and a tracker housing configured to engage with the base engagement panel to enclose the PCB, the plurality of sensors, the MCU, the plurality of switching components, and the rechargeable battery, wherein a subset of the plurality of sensors are activated when the tracker is coupled to the first base unit causing at least one of the plurality of first trigger columns to extend through at least one of the plurality of column ports and actuate at least one of the plurality of switching components.

16. The method of claim 15, further comprising:

detaching the tracker from the first base unit;

coupling a second equipment engagement side of a second base unit to a portion of a second exercise apparatus, wherein the second base unit further comprises a second tracker engagement side opposite the second equipment engagement side and the second tracker engagement side comprises a plurality of second attachment arms, a second tracker engagement side, and a plurality of second trigger columns arranged on the second tracker engagement side in a second arrangement different from the first arrangement; and coupling the tracker to the second base unit by securing the tracker with the plurality of second attachment arms, wherein another subset of the plurality of sensors are activated when the tracker is coupled to the second base unit causing at least one of the plurality of second trigger columns to extend through at least one of the plurality of column ports and actuate at least one of the plurality of switching components.

17. The method of claim 15, further comprising storing data collected by the plurality of sensors in a memory unit of the tracker and transmitting data collected by the plurality of sensors to a client device using a wireless communication unit of the tracker.

18. The method of claim 15, further comprising rotating the tracker clockwise or counterclockwise with respect to the first base unit to actuate different switching components and different sensors, wherein at least one of the trigger columns on the first base unit is aligned with one of the column ports on the tracker and the at least one of the trigger columns on the first base unit is aligned with another one of the column ports on the tracker when the tracker is rotated with respect to the first base unit.

19. The method of claim 15, wherein the plurality of sensors comprises any combination of a multi-axis inertial motion sensor, an optical heart rate sensor, a galvanic skin response (GSR) sensor, a bio-impedance sensor, an ambient light sensor, and a UV sensor.

20. The method of claim 15, further comprising depressing at least one of the first trigger columns into the first tracker engagement side using the base engagement panel of the tracker.

* * * * *